(12) United States Patent
Graumann

(10) Patent No.: US 9,345,440 B2
(45) Date of Patent: May 24, 2016

(54) APPARATUS AND METHOD FOR POSITIONING A MEDICAL DEVICE

(71) Applicant: SIEMENS AKTIENGESELLSCHAFT, Munich (DE)

(72) Inventor: Rainer Graumann, Hoechstadt (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 137 days.

(21) Appl. No.: 14/033,723

(22) Filed: Sep. 23, 2013

(65) Prior Publication Data
US 2014/0086393 A1    Mar. 27, 2014

(30) Foreign Application Priority Data
Sep. 21, 2012  (DE) .......................... 10 2012 217 072

(51) Int. Cl.
A61B 6/00    (2006.01)
A61B 6/04    (2006.01)

(52) U.S. Cl.
CPC ............. A61B 6/4405 (2013.01); A61B 6/4441 (2013.01); A61B 6/4458 (2013.01); A61B 6/4464 (2013.01); A61B 6/547 (2013.01); A61B 6/0457 (2013.01)

(58) Field of Classification Search
USPC .......................... 378/193, 195, 196, 197, 198
See application file for complete search history.

(56) References Cited

U.S. PATENT DOCUMENTS

| 2009/0148023 A1 | 6/2009 | Spahn |
| 2010/0008474 A1* | 1/2010 | Hornung et al. .............. 378/197 |
| 2012/0029694 A1 | 2/2012 | Muller |

FOREIGN PATENT DOCUMENTS

| CN | 101655984 A | 2/2010 |
| DE | 102010034678 A1 | 1/2012 |
| DE | 102010038800 A1 | 2/2012 |
| DE | 202012004601 U1 | 6/2012 |

* cited by examiner

Primary Examiner — Nicole Ippolito
Assistant Examiner — Hanway Chang
(74) Attorney, Agent, or Firm — Laurence Greenberg; Werner Stemer; Ralph Locher

(57) ABSTRACT

A mobile C-arm is able to be positioned in a predetermined alignment by a positioning unit and an associated method. The apparatus has a positioning unit containing a controllable section having at least a first hinged bracket and a first hinge and is able to be positioned with a removable connection to the medical device at a determinable location. The medical device is able to be positioned at a predetermined location by means of the positioning unit.

10 Claims, 1 Drawing Sheet

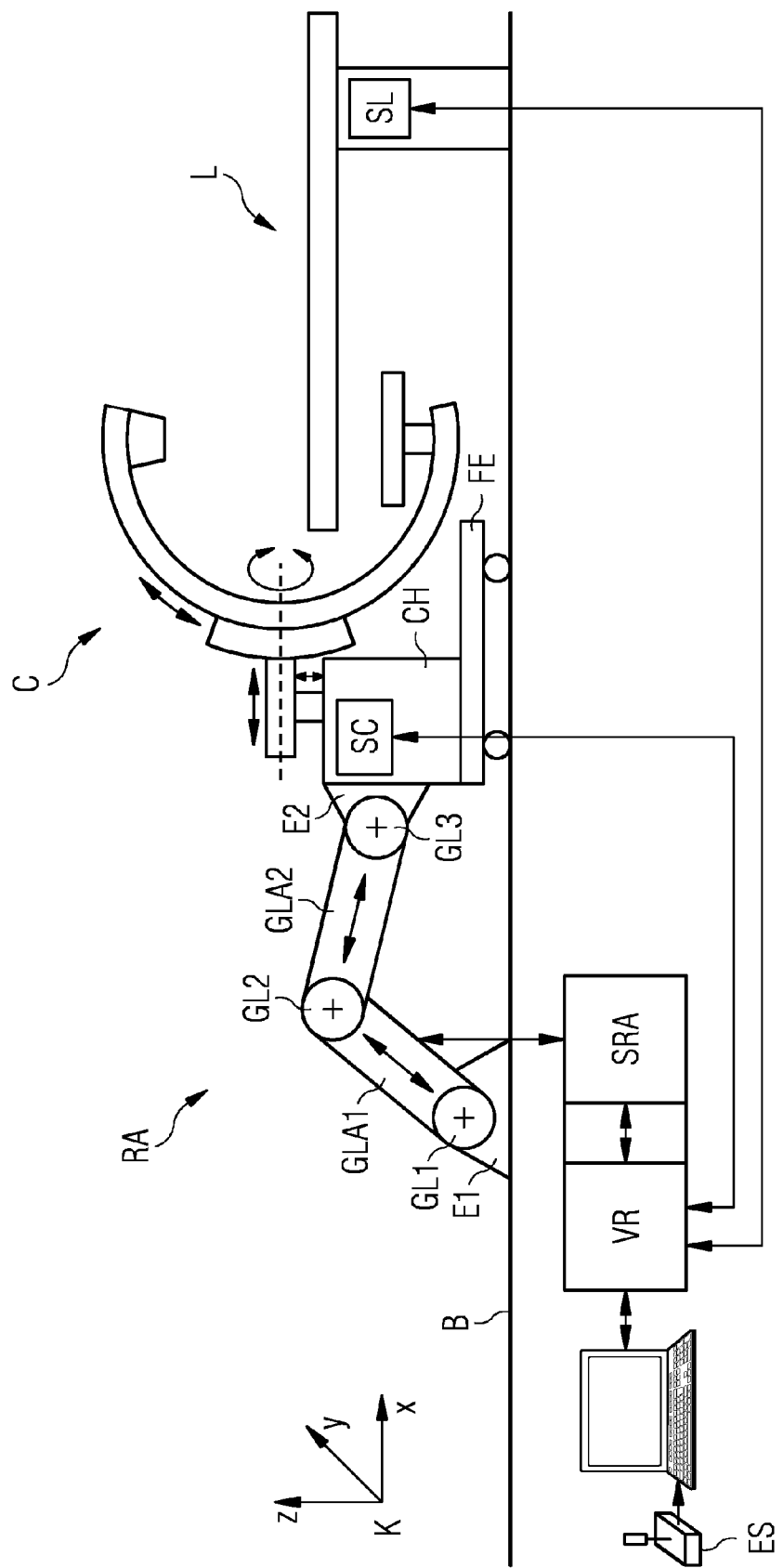

APPARATUS AND METHOD FOR POSITIONING A MEDICAL DEVICE

CROSS-REFERENCE TO RELATED APPLICATION

This application claims the priority, under 35 U.S.C. §119, of German application DE 10 2012 217 072.3, filed Sep. 21, 2012; the prior application is herewith incorporated by reference in its entirety.

BACKGROUND OF THE INVENTION

Field of the Invention

The invention relates to an apparatus and a method for positioning device units, in particular for positioning mobile C-arms.

Device units, in particular medical devices such as mobile C-arms for example, are manually pushed or driven to a destination for X-ray imaging, such as an operating table or a patient couch for example. Following a sequence of X-rays or one single X-ray, the mobile C-arm is moved from a usage location to a parking position located within a treatment room, or to a locality adjacent to a treatment room. During a treatment or following a procedure, the mobile C-arm suitable for taking X-rays is pushed to its usage location in order to be able to document or evaluate the progress of treatments or operations, or to find solutions for surgery-related questions. A repeated use of the C-arm is problematic in that previously occupied positions and alignments can only be reached again intuitively by the operating personnel. A continuous positioning of the C-arm for individual X-rays of a panorama image requires an increased time outlay by operating personnel for each positioning of the mobile C-arm.

SUMMARY OF THE INVENTION

It is accordingly an object of the invention to provide an apparatus and a method for positioning a medical device which overcome the above-mentioned disadvantages of the prior art methods and devices of this general type, in such a way that the medical device can be positioned precisely therewith.

The inventive apparatus and the corresponding method of positioning a medical device contains a positioning unit having at least one controllable section which has at least a first hinged bracket and a first hinge wherein the positioning unit is able to be connected to a medical device and the medical device is able to be positioned in a determinable location.

The invention is advantageous in that the mobility of the C-arm is maintained on the one hand, and on the other hand a reproducible positioning of the mobile C-arm can be carried out in a machine-controlled manner.

The invention is advantageous in that the medical device is able to be positioned at a predetermined location in the room.

The invention is advantageous in that the mobile C-arm unit is able to be moved parallel to the operating table or patient couch.

Aside from the advantage of being able to use the C-arm at a plurality of usage locations, the invention is also advantageous in that the C-arm is able to be placed at a predetermined location by the controllable positioning unit.

The invention is advantageous in that the coordinate data from the positioning unit can also be used to create panoramic images.

The invention is advantageous in that, by combining an orbital rotation with a simultaneous continuous longitudinal displacement of the mobile C-arm, an expanded 3D image of an elongated object may be created.

The invention is advantageous in that the generator unit can be transferred from the C-arm of the mobile C-arm, thus making the C-arm more flexible in terms of use.

The invention is advantageous in that, in connection with a control system of the C-arm, the control unit of the positioning unit facilitates a precise and optimized positioning of the C-arm.

The invention is advantageous in that the degrees of freedom of the C-arm, the positioning unit and a couch unit receiving the patient can be selected, matched to one another and added.

The invention is advantageous in that the alignment of the wheels of the mobile C-arm is able to be coupled with the alignment of the positioning unit.

In the apparatus and the corresponding method, the mobile C-arm is able to be connected to a positioning unit, the positioning unit being able to position the C-arm in a predeterminable alignment Other features which are considered as characteristic for the invention are set forth in the appended claims.

Although the invention is illustrated and described herein as embodied in an apparatus and a method for positioning a medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The single FIGURE of the drawing is an illustration showing a device concept along with its individual components according to the invention.

DETAILED DESCRIPTION OF THE INVENTION

Referring now to the single FIGURE of the drawing in detail, there is shown the individual components for a positioning unit RA, a medical device such as a mobile C-arm C for instance and a further medical device, such as a couch unit L for instance. A first control unit SRA is assigned to the positioning unit RA, a second control unit SC is assigned to the mobile C-arm C and a third control unit SL is assigned to the couch L unit. By the first, second and third control units SRA, SC, SL, the individual components of the positioning unit RA, the mobile C-arm C and the couch unit L can be positioned separately or together by a network computer VR assigned to the positioning unit RA for instance.

The positioning unit RA has a controllable section having at least a first hinged bracket GLA1 and at least a first hinge GL1. The controllable section is completed by a first and second connection element E1, E2. The FIGURE shown features a first and second hinged bracket GLA1, GLA2. The first hinged bracket GLA1 is connected to the second hinged bracket GLA2 via a second hinge GL2. The first and second hinged brackets GLA1, GLA2 can be embodied as telescope-like. The first hinged bracket GLA1 is connected to a first hinge GL1 with the first connection element E1 and the second hinged bracket GLA2 is connected to a third hinge G3 with the second connection element E2. The first, second and third hinges GL1, GL2, GL3 each have at least one degree of freedom. The first connection element E1 is able to be connected by its free end to stationary or flexible elements in the operating room, for instance. The first connection element E1 can be removably mounted to anchor points provided in the floor region B of the treatment room for instance. The first connection element E1 can also be mounted on rail elements which are by way of example integrated into the floor of the operating or treatment room. The mounting location for the free end of the first connection element E1 of the positioning unit RA provided in the floor, wall or ceiling area can be embodied with suction elements by way of example. The first connection element E1 of the positioning unit RA can be arranged or positioned at any position in the treatment or operating room by the suction elements. The second connection unit E2 is removably connected to a chassis CH of the mobile C-arm C by its free end via a defined interface. The position coordinates of the connection elements E1, E2 as well as the hinged brackets GLA1, GLA2 and the positioning of the first, second and third hinges GL1, GL2, GL3 can be determined via electromagnetic or optical sensors by way of example, and used for orienting or aligning the mobile C-arm C. Thus the coordinates of the position coordinates in each case could be determined or transmitted using RFID technology, by way of example.

The first hinge GL1, the second hinge GL2 and the third hinge GL3, as well as the first and second hinged brackets GLA1, GLA2 can be individually controlled by the first control unit SRA provided for the positioning unit RA. The first, second and third hinges GL1, GL2 and GL3 are embodied such that translational and also rotational movements of the positioning unit RA can be realized. In order to increase the movement radius of the positioning unit RA about an anchoring point in the floor, wall or ceiling area, the first hinged bracket GL1 and/or the second hinged bracket GL2 can be embodied as having telescope-like elements.

The first control apparatus SRA of the positioning unit RA, the second control unit SC of the mobile C-arm C and the third control unit SL of the couch unit L are connected via a network computer VR. The individual components of the positioning unit RA, the C-arm C and the couch unit L can be controlled and positioned by the network computer VR so that the imaging unit of the C-arm, made up of an X-ray source and a detector, has an optimal position or alignment in relation to an object to be imaged for each X-ray. A trajectory for a series of X-rays including all controllable components can also be defined and launched by the network computer VR. Thus for example a 3D data record, made up of a plurality of 2D X-ray images, can be created via a combination of orbital rotations and/or angular rotations of the C-arm with a continuous change in length of the first and second hinged brackets GLA1, GLA2 of the positioning unit RA. User interface functionalities for an improved positioning of the C-arm and for optimal and precise repositioning can also be integrated by the network computer VR. In this way, the alignment of the wheels of the mobile C-arm can be coupled with the alignment of the positioning unit. A sequence of individual X-ray images along a patient axis is likewise possible. In connection with the first control unit SRA of the positioning unit RA and the second control unit SC of the mobile C-arm, the third control unit SL can be made to operatively connect with the couch unit L via the network computer VR. In addition to a free movement of the positioning unit RA, the couch could be driven continuously horizontally and/or vertically for example. This is advantageous in that a repositioning is carried out more quickly for example and therefore X-ray images are able to be created more quickly. If, by way of example, the position of the C-arm or the position of the X-ray source and the detector unit is known to the network computer VR, then a precise repositioning of the C-arm can be carried out and further X-rays of patients can be recorded.

The C-arm of the mobile C-arm is connected to the drivable chassis CH via hinges. These hinges allow the C-arm, along with the X-ray source and the detector, to be moved orbitally and angularly as well as rotationally, in terms of its height and in a pivoted fashion. The chassis CH of the mobile C-arm is provided with a drivable unit FE. The drivable unit FE can have movable rolling elements which can be manually controlled or controlled by motor, possibly by electric motors, with which the C-arm can be moved to any position. By the network computer VR and its ability to controllably intervene in the second control unit SC of the mobile C-arm C, the orientation of the wheels of the mobile C-arm C can be determined. Docking elements for the second connection element E2 of the positioning unit RA are arranged on at least one side of the chassis.

The positioning unit RA can also be equipped with a generator which takes over the power supply of the X-ray source and the detector of the C-arm. This is advantageous in that the C-arm can be configured more easily and thus will be more stable during a rotation.

The positioning unit RA can be removably connected to its first connection element E1 at a fixed location in the room for instance. The positioning unit RA can then accurately position the mobile C-arm from this starting location, for instance by control signals emitted by an electronic control unit ES. The positioning unit RA in a resting position could also initially dock with a mobile C-arm likewise in a resting position and then drive the C-arm from the resting position to a desired position, to an operating table, for example. In a further exemplary application, the positioning unit RA could be connected to the mobile C-arm and the mobile C-arm with the positioning unit could initially be moved to a predetermined place in order to then position the C-arm in a precise way with the aid of said positioning unit RA fixed in the floor region.

The invention claimed is:

1. An apparatus for positioning a medical device, the apparatus comprising:
   a medical device;
   a unit including rollable elements for supporting said medical device on a floor;
   a positioning unit including a controllable section having at least a first hinged bracket and a first hinge and able to be positioned with a removable connection to said medical device at a predetermined location; and
   a connection element for supporting said positioning unit on the floor, wherein said medical device is not supported on the floor by said connection element;
   said positioning unit configured for positioning said medical device and said unit at a predetermined location while said medical device is supported by said rollable elements of said unit.

2. The apparatus according to claim 1, wherein said controllable section is able to be connected to the determinable location at a first end having a first connection unit and connected to the medical device at a second end having a second connection unit.

3. The apparatus according to claim 2, wherein said first connection unit has corresponding connection elements which are able to be connected at a determinable location of a room and is able to be connected removably.

4. The apparatus according to claim 2, wherein said positioning unit has a second hinged bracket, and at least one bracket selected from the group consisting of said first hinged bracket and said second hinged bracket includes telescoping elements.

5. The apparatus according to claim 1, wherein said positioning unit is able to be positioned freely.

6. The apparatus according to claim 1, wherein said controllable section has said first hinge at a first end and a second hinge at a second end.

7. The apparatus according to claim 1, wherein said positioning unit further has a first control unit, the medical device has a second control unit, a further medical facility has a third control unit, the first, second and third control units are connected via a network computer which initiates control signals for coordinated changes in position.

8. The apparatus according to claim 1, wherein the medical device is a mobile C-arm having an alignable X-ray source and a detector unit which is able to be aligned thereto.

9. A method for positioning a medical device, which comprises the step of:

providing a medical device, a unit including rollable elements for supporting the medical device on a floor, a positioning unit, and a connection element supporting the positioning unit on the floor, wherein the medical device is not supported on the floor by the connection element, and wherein the positioning unit includes a controllable section having at least a first hinged bracket and a first hinge and able to be positioned with a removable connection to a medical device at a predetermined location;

with the positioning unit, positioning the medical device and the unit at a predetermined location while the medical device is supported by the rollable elements of the unit.

10. The method according to claim 9, which further comprises initiating control signals for tunable changes in position by a network computer between the positioning unit and a patient positioned on a couch unit, wherein the medical device is a mobile C-arm.

* * * * *